(12) United States Patent
Horner et al.

(10) Patent No.: US 9,168,092 B2
(45) Date of Patent: Oct. 27, 2015

(54) SURGICAL INSTRUMENT WITH PROTECTIVE SHEATH

(75) Inventors: Shawn K. Horner, Woods Cross, UT (US); Ryan D. Lewis, Cedar Hills, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 1111 days.

(21) Appl. No.: 13/029,434

(22) Filed: Feb. 17, 2011

(65) Prior Publication Data

US 2012/0215217 A1  Aug. 23, 2012

(51) Int. Cl.
*A61B 18/14* (2006.01)
*A61B 18/00* (2006.01)
*A61B 18/04* (2006.01)

(52) U.S. Cl.
CPC ..... *A61B 18/148* (2013.01); *A61B 2018/00083* (2013.01); *A61B 2018/00595* (2013.01); *A61B 2018/00607* (2013.01); *A61B 2018/046* (2013.01); *A61B 2018/1407* (2013.01); *A61B 2018/1412* (2013.01); *A61B 2018/1417* (2013.01); *A61B 2018/1425* (2013.01)

(58) Field of Classification Search
USPC .............................................. 606/41, 45–50
See application file for complete search history.

(56) References Cited

U.S. PATENT DOCUMENTS

| | | | |
|---|---|---|---|
| 4,161,950 A * | 7/1979 | Doss et al. | 606/48 |
| 4,228,800 A * | 10/1980 | Degler et al. | 606/48 |
| 4,324,044 A | 4/1982 | Shahinian, Jr. | |
| 4,569,133 A | 2/1986 | Schmidt | |
| 5,100,402 A | 3/1992 | Fan | |
| 5,244,462 A | 9/1993 | Delahuerga et al. | |
| 5,324,288 A | 6/1994 | Billings et al. | |
| 5,382,247 A | 1/1995 | Cimino et al. | |
| 5,800,378 A | 9/1998 | Edwards et al. | |
| 5,810,764 A | 9/1998 | Eggers et al. | |
| 5,833,689 A * | 11/1998 | Long | 606/48 |
| 5,846,237 A * | 12/1998 | Nettekoven | 606/41 |
| 6,149,646 A | 11/2000 | West, Jr. et al. | |
| 6,193,715 B1 | 2/2001 | Wrublewski et al. | |
| 6,494,881 B1 | 12/2002 | Bales et al. | |
| 6,497,705 B2 * | 12/2002 | Comben | 606/41 |
| 6,533,781 B2 * | 3/2003 | Heim et al. | 606/45 |
| 7,335,198 B2 | 2/2008 | Eggers et al. | |
| 7,727,232 B1 * | 6/2010 | Maurer et al. | 606/48 |
| 7,749,221 B2 | 7/2010 | Rontal | |
| 2008/0027428 A1 * | 1/2008 | Palanker et al. | 606/45 |
| 2008/0140066 A1 * | 6/2008 | Davison et al. | 606/37 |

* cited by examiner

*Primary Examiner* — Michael Peffley
(74) *Attorney, Agent, or Firm* — Workman Nydegger (57) ABSTRACT

An electrode tip for use in performing electrosurgical operative procedures is disclosed. The electrode tip includes a main body that can receive electrical energy from an electrosurgical generator. The main body includes a working surface that communicates the electrical energy to patient tissue during the operative procedure. An insulative sheath is disposed around a portion of the electrode tip to prevent electrical energy from being communicated from the covered portions of the electrode tip to patient tissue. The insulative sheath has a leading edge that is shaped to minimize resistance to the movement of the electrode tip through patient tissue. The leading edge can be arcuately shaped or angled relative to a longitudinal axis of the electrode tip to provide the resistance reducing characteristics.

25 Claims, 9 Drawing Sheets

SURGICAL INSTRUMENT WITH PROTECTIVE SHEATH

BACKGROUND OF THE INVENTION

1. The Field of the Invention

This invention relates to the field of surgery. More particularly, the invention relates to surgical instruments that facilitate the performance of surgery with less resistance to the movement of the surgical instruments during the performance of surgical procedures.

2. The Relevant Technology

As is known to those skilled in the art, modern surgical techniques often employ radio frequency (RF) power to cut tissue and coagulate bleeding encountered in performing surgical procedures. For a historical perspective and details of such techniques, reference is made to U.S. Pat. No. 4,936,842, issued to D'Amelio et al., and entitled "Electroprobe Apparatus," the disclosure of which is incorporated by this reference.

Electrosurgery is widely used and offers many advantages including the use of a single surgical instrument for both cutting and coagulation. A monopolar electrosurgical generator system has an active electrode, such as in the form of an electrosurgical instrument having a hand piece and a conductive electrode or tip, that is applied by the surgeon to the patient at the surgical site to perform surgery, and a return electrode to connect the patient back to the generator. The electrode or tip of the electrosurgical instrument is small at the point of contact with the patient to produce an RF current with a high current density in order to produce a surgical effect of cutting or coagulating tissue. The return electrode carries the same RF current provided to the electrode or tip of the electrosurgical instrument, thus providing a path back to the electrosurgical generator.

Some active electrodes are modified with a protective sheath which prevents inadvertent contact between portions of the electrode and tissue, limits depth of penetration into the tissue, and can also provide a tighter fit when the electrode is engaged in the electrosurgical pencil. The distal end of the protective sheath in past configurations is not well suited for electrosurgical incisions. Incisions with an electrosurgical instrument are made on an angle due to the natural position in the surgeon's hand, which causes the edge of the protective sheath to engage the tissue in such a way that friction is created between the sheath and the tissue. This friction creates drag that distorts the tissue being addressed and results in bunching of the tissue and distortion of the incision. Such distortion often takes the form of a scalloped edge or beveled edge that makes reaproximation of the tissue edges during suturing difficult and results in poor cosmetic outcomes. A precise incision is particularly important where the skin is thinner and more delicate, such as on the face and around the eyes. Drag also leads to fatigue in a surgeon's hand, a major contributor to repetitive use injuries. Fatigue also contributes to loss of fine motor control and subsequently diminishes the surgeon's ability to operate as precisely as desired.

Therefore, it would be an advantage to have an electrode with an insulative sleeve that provides a desired insulative barrier between a portion of the electrode and the patient's tissue, while at the same time limiting the amount of drag or resistance resulting from tissue getting caught on the leading edge of the insulative sleeve. The subject matter claimed herein, however, is not limited to embodiments that solve any disadvantages or that operate only in environments such as those described above. Rather, this background is only provided to illustrate one exemplary technology area where some embodiments described herein may be practiced.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF THE INVENTION

Generally, the present invention relates to an electrosurgical instrument that facilitates the performance of electrosurgery while reducing resistance to the movement of the electrosurgical instrument through a patient's tissue. Reducing resistance to the movement of the electrosurgical instrument through the patient's tissue can reduce fatigue experienced in a physician's hand, increase the accuracy and ease of performing electrosurgical procedures, and improve the effectiveness and efficiency of the electrosurgical instrument.

In one aspect of the disclosure, a surgical device is adapted for use in performing surgical operative procedures and includes a main body and a sheath.

In another aspect that may be combined with any of the aspects herein, the main body is formed of a conductive material.

In another aspect that may be combined with any of the aspects herein, the main body has a first side, a second, opposing side, and at least one working surface adapted to be applied to patient tissue for performing operative procedures thereupon.

In another aspect that may be combined with any of the aspects herein, the sheath is disposed around a portion of the main body.

In another aspect that may be combined with any of the aspects herein, the sheath has a leading edge that forms a generally obtuse angle with the at least one working surface.

In another aspect that may be combined with any of the aspects herein, the at least one working surface includes a first working surface disposed on the first side of the main body and a second working surface disposed on the second, opposing side of the main body.

In another aspect that may be combined with any of the aspects herein, the sheath includes a first side disposed adjacent to the first side of the main body and a second side disposed adjacent the second, opposing side of the main body.

In another aspect that may be combined with any of the aspects herein, the leading edge of the sheath extends between the first and second sides of the sheath.

In another aspect that may be combined with any of the aspects herein, the leading edge of the sheath has a general shape that is at least one of arcuate, elliptical, triangular, trapezoidal, or polygonal.

In another aspect that may be combined with any of the aspects herein, the leading edge includes a first end disposed adjacent the first side of the main body, a second end disposed adjacent the second side of the main body, and at least one peak disposed between the first and second ends.

In another aspect that may be combined with any of the aspects herein, the main body has a longitudinal axis and the at least one peak is axially offset along the longitudinal axis from the first and second ends of the leading edge.

In another aspect that may be combined with any of the aspects herein, the first and second ends of the leading edge are axially offset from one another along the longitudinal axis.

In another aspect that may be combined with any of the aspects herein, the leading edge has a radius of between about 0.060 inches and about 0.200 inches.

In another aspect that may be combined with any of the aspects herein, the leading edge has a radius of between about 0.075 inches and about 0.125 inches.

In another aspect that may be combined with any of the aspects herein, the at least one peak is axially offset along the longitudinal axis from the first and second ends of the leading edge by a distance of between about 0.015 inches and about 0.029 inches.

In another aspect that may be combined with any of the aspects herein, the at least one peak is axially offset along the longitudinal axis from the first and second ends of the leading edge by a distance of between about 0.009 inches and about 0.052 inches.

In another aspect that may be combined with any of the aspects herein, the first end of the leading edge forms a generally obtuse angle with the first working surface and the second end of the leading edge forms a generally obtuse angle with the second working surface.

In another aspect that may be combined with any of the aspects herein, the main body has a longitudinal axis and the leading edge extends across the main body from the first side to the second, opposing side, and the leading edge forms a generally obtuse angle with the longitudinal axis.

In another aspect that may be combined with any of the aspects herein, the leading edge includes a first end that forms a generally obtuse angle with the at least one working surface.

In another aspect that may be combined with any of the aspects herein, the at least one working surface comprises a first working surface disposed on the first side of the main body and a second working surface disposed on the second, opposing side of the main body, and the leading edge includes a first section that forms a generally obtuse angle with the first working surface and a second section that forms a generally obtuse angle relative to the second working surface.

In another aspect that may be combined with any of the aspects herein, the first section and the second section of the leading edge are oriented generally transversely to one another.

In another aspect that may be combined with any of the aspects herein, the sheath if formed of PTFE.

In another aspect that may be combined with any of the aspects herein, the sheath is formed of an electrically insulative material.

In another aspect that may be combined with any of the aspects herein, the leading edge is asymmetrical across a longitudinal axis of the surgical device.

In another aspect that may be combined with any of the aspects herein, the sheath has a first side disposed adjacent the first working surface, a second side disposed adjacent the second working surface, and a leading edge extending between the first and second sides, with the leading edge having a generally arcuate shape such that a first end of the leading edge forms a generally obtuse angle with the first working surface and a second end of the leading edge forms a generally obtuse angle with the second working surface.

In another aspect that may be combined with any of the aspects herein, the leading edge includes at least one peak that is offset from the first and second ends of the leading edge along a longitudinal axis of the electrode tip.

In another aspect that may be combined with any of the aspects herein, the at least one peak is offset from the first and second ends of the leading edge by a distance of about 0.015 inches and the leading edge has a radius of about 0.125 inches.

In another aspect that may be combined with any of the aspects herein, the first and second opposing sides of the main body define respective first and second working surfaces that are adapted to communicate the electrical energy from the main body to patient tissue for performing electrosurgical operative procedures thereupon In another aspect that may be combined with any of the aspects herein, the main body has a longitudinal axis.

In another aspect that may be combined with any of the aspects herein, the leading edge of the sheath extends between the first and second sides of the sheath and across the main body, forming a generally obtuse angle with the longitudinal axis.

In another aspect that may be combined with any of the aspects herein, the leading edge includes a first end disposed adjacent the first working surface, the first end and the first working surface forming a generally obtuse angle.

This Brief Summary is provided to introduce a selection of concepts in a simplified form that are further described below in the Detailed Description. This Brief Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

The present invention relates generally to surgical devices. More specifically, the present invention relates to surgical instruments that facilitate the performance of surgery with less resistance to the movement of the surgical instruments during the performance of surgical procedures. The surgical devices of the present invention may take a variety of forms or may be part of a variety of different types of surgical systems. These various types of surgical devices and systems may include energy based devices and systems, including electrosurgical devices and systems, thermal or fluid based devices and systems, or mechanical based systems, including scalpels and the like.

According to one exemplary embodiment, an electrosurgical instrument includes a hand piece that holds an electrode tip in one end thereof and is connected to an electrosurgical generator for receiving electrical energy therefrom. The electrode tip includes an insulative sheath disposed about at least a portion of a working end while leaving a portion of the working end exposed to enable the performance of electrosurgery. The insulative sheath has a leading edge that is shaped or contoured to avoid tissue being caught on the leading edge or between the leading edge and the exposed portion of the electrode tip's working end. Avoiding the catching of tissue on the leading edge of the insulative sheath can improve the performance of the electrode tip. For instance, reducing friction between the tissue and the sheath prevents the tissue from bunching and distorting the incision, thereby creating more precise incisions that are more easily reaproximated for better cosmetic outcomes. Additionally, reducing friction between the sheath and the tissue reduces fatigue in the surgeon's hand, which can enable the surgeon to maintain fine motor control throughout surgical procedures.

Reference will now be made to the drawings to describe various aspects of exemplary embodiments of the invention. It is understood that the drawings are diagrammatic and schematic representations of such exemplary embodiments, and are not limiting of the present invention, nor are any particular elements to be considered essential for all embodiments or that elements be assembled or manufactured in any particular order or manner. No inference should therefore be drawn from the drawings as to the necessity of any element. In the following description, numerous specific details are set forth in order to provide a thorough understanding of the present invention. It will be obvious to one of ordinary skill in the art, however, that the present invention may be practiced without these specific details. In other cases, well known aspects of surgical systems, devices, and methods, and general manufacturing techniques are not described in detail herein in order to avoid unnecessarily obscuring the novel aspects of the present invention.

FIGS. 1-15 and the following discussion are intended to provide a brief general description of exemplary devices in which embodiments of the invention may be implemented. While electrodes for electrosurgical systems are described below, these are but a few examples, and embodiments of the invention may be implemented with other types of systems or devices, including other types of energy based systems as well as mechanical systems. Accordingly, throughout the specification and claims, the phrases "electrode," "electrosurgical electrode," "electrode blade," "electrode tip," and the like are intended to apply broadly to any type of item that can be used to perform a surgical procedure as described herein. More specifically, the present invention may be employed or incorporated in energy based surgical systems, including thermal based surgical systems and fluid based surgical systems, or mechanical based surgical systems, including scalpels and the like.

Figure 1:
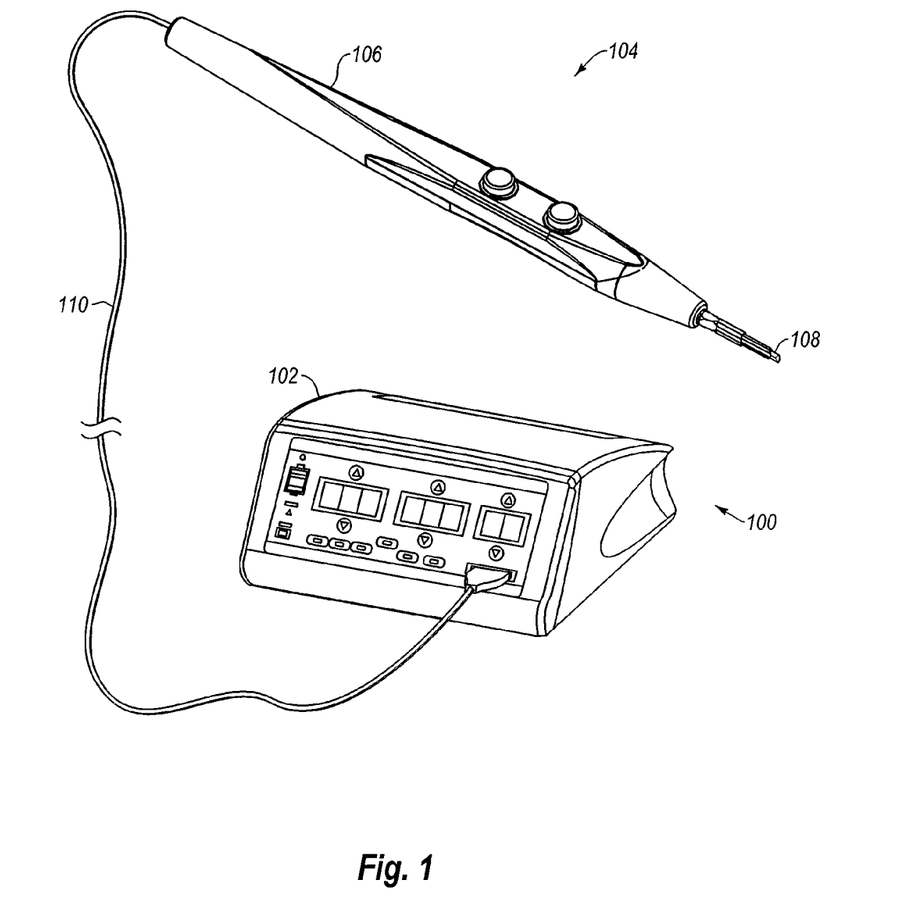
FIG. 1 illustrates an electrosurgical system with an electrosurgical instrument according to one exemplary embodiment of the present invention.

FIG. 1 and the corresponding discussion are intended to provide a brief, general description of one exemplary operating system in which embodiments of the invention may be implemented. Although not required, the invention will be described in the general context of providing specific properties, attributes, and/or characteristics to an electrosurgical electrode in order to improve the quality of electrosurgical operations and limit resistance or drag as the electrode moves through the tissue of a patient during electrosurgery.

Referring to FIG. 1, an exemplary system is illustrated that can include the features of the present invention. In FIG. 1, electrosurgical system 100 is illustrated, which includes a wave generator 102 and an electrosurgical instrument 104. Electrosurgical instrument include a hand piece 106 and an electrode tip 108. Generator 102, in a preferred embodiment, is an RF wave generator. A surgeon may use electrosurgical system 100 during surgical procedures to cut tissue and/or cauterize blood vessels of a patient's body.

In electrosurgery, radio frequency (RF) electrical energy is produced by a wave generator, such as wave generator 102, and is introduced to a patient's body by an electrosurgical instrument, such as electrosurgical instrument 104, which is electrically coupled to wave generator 102 and includes electrode tip 108. Wave Generator 102 can include a high-frequency oscillator and amplifiers to generate an RF electrical energy wave that can be used to cut tissue and/or cauterize blood vessels during electrosurgery. The RF electrical energy wave powers electrosurgical instrument 104 and is transmitted from wave generator 102 to electrosurgical instrument 104 via cord 110. An electrical discharge is delivered from electrode tip 108 to the patient in order to cause the heating of cellular matter of the patient that is in close contact to electrode tip 108. The heating takes place at an appropriately high temperature to allow electrosurgical instrument 104 to be used to perform electrosurgery. A grounding electrode (not shown) provides a return electrical path to wave generator 102 for any excess charge that is dissipated into surrounding tissue of the patient's body.

During electrosurgery, electrosurgical instrument 104 may be used to independently or concurrently cut and cauterize. A constant sinusoidal wave supplied by wave generator 102 and transmitted to electrosurgical instrument 104 allows electrode tip 108 to cut through tissue of the patient's body.

Alternatively, a damped wave supplied by wave generator 102 and transmitted to electrosurgical instrument 104 allows electrode tip 108 to cauterize leaking blood vessels and/or tissues. A combination of the constant sinusoidal wave and the damped wave can be supplied by wave generator 102 to electrosurgical instrument 104 for allowing electrode tip 108 to concurrently cut and cauterize, thereby minimizing tissue trauma and blood loss during the surgical procedure.

With attention to FIGS. 2-7, various views of electrode tip 108 are illustrated. As seen in the Figures, electrode tip 108 includes a main body having a connection end 112 and a working end 114. At least a portion of connection end 112 is typically exposed so that a direct electrical connection can be made between connection end 112 and hand piece 106. Electrical discharge is delivered to the patient's body from working end 114, which in the illustrated embodiment is a shaped or sharpened blade-type electrode tip. That is, working end 114 has two opposing major surface 116A, 116B that taper closer together to form two generally parallel, shaped or sharpened working surfaces 118A, 118B. The end of electrode tip 108 can also be formed into a working surface 118C.

Figure 2:
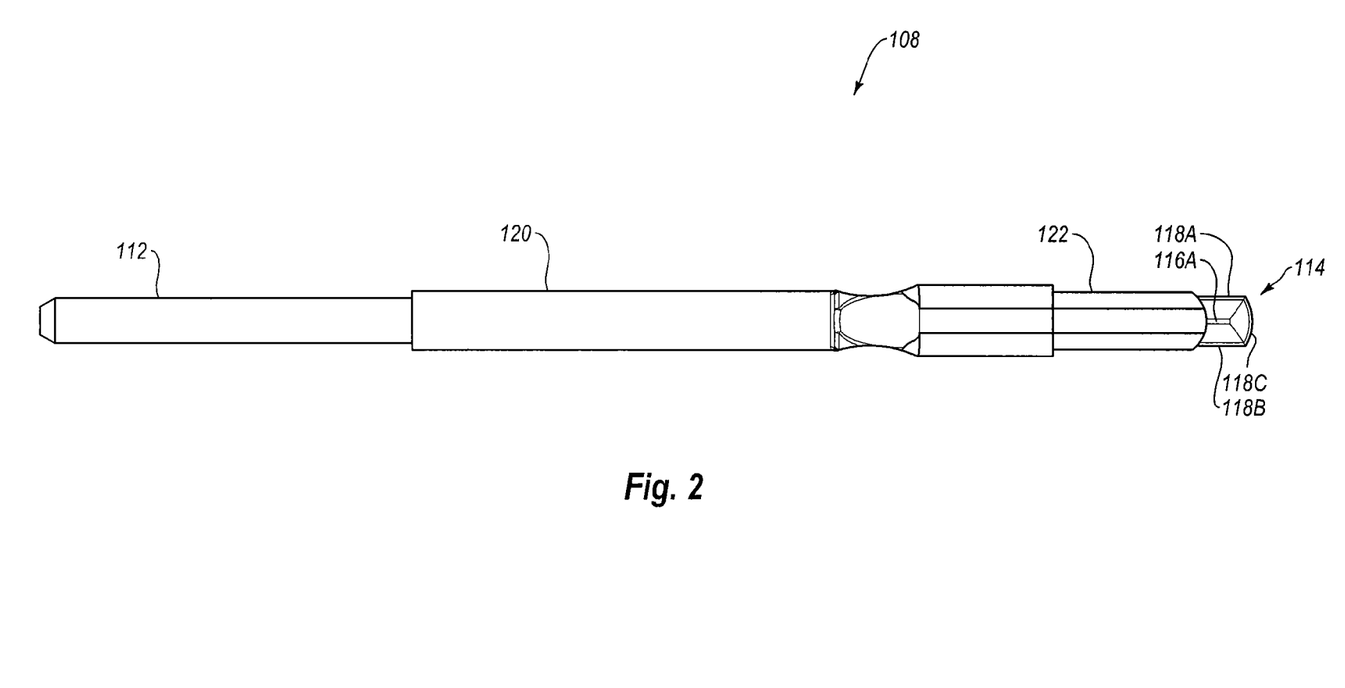
FIG. 2 illustrates a top view of an exemplary embodiment of an electrode tip for use in the electrosurgical system of FIG. 1 to cut tissue and cauterize blood vessels.

While electrode tip 108 is illustrated with a sharpened or shaped working end 114, it will be understood that the present invention may be practiced with other types of electrode tips. For instance, the electrode tip may include two generally parallel major surfaces and two generally parallel working surfaces, with the working surfaces not being shaped or sharpened. In other embodiments, electrode tip may take the form of a scalpel-type electrode tip, a needle electrode, a loop electrode, a modified ball electrode, and various laparoscopic electrodes. In any case, the electrode tip can create an incision similar to a traditional scalpel. Rather than employing a mechanical action for cutting through tissue as is done with a scalpel, however, the electrical discharge allows the working end of the electrode tip to slide through the tissue as the tissue is being superheated to an appropriate temperature to perform the electrosurgical procedure.

Electrode tip 108 can be formed of stainless steel so as to readily conduct electrical energy. A sleeve fitting 120 may be positioned around at least a portion of connection end 112, and optionally part of working end 114, to provide protection and to facilitate coupling of electrode tip 108 to hand piece 106. Further, a coating of non-stick and/or insulating material may cover the surface of electrode tip 108. Such a coating may serve to eliminate or reduce the clinging of charred tissue to electrode tip 108 and/or facilitate capacitive coupling of electrode tip 108 to the patient's tissue. Non-stick materials suitable for use as a coating on electrode tip 108 may include, but are not limited to, polytetrafluoroethylene ("PTFE") or a hybrid material that can include a combination of at least one of an organic material and an inorganic material, and that provides the coated surface with desirable properties, such as a high temperature stability, flexibility, and a low temperature application condition so that the coating layer may be applied by a spray or dip process. An example of a hybrid coating is provided in U.S. Pat. No. 6,951,559, entitled "Utilization of a Hybrid Material in a Surface Coating of an Electrosurgical Instrument," that issued on Oct. 4, 2005 to Greep, the disclosure of which is incorporated herein by reference in its entirety.

An insulative sheath 122 is also advantageously disposed on a portion of electrode tip 108. In the illustrated embodiment, insulative sheath 122 covers a portion of working end 114 in order to provide an insulative barrier between the covered portion of working end 114 and the patient's tissue. Insulative sheath 122 allows for the exposed portion of working end 114 to be used to perform electrosurgery without communicating electrical energy across insulative sheath 122 between the covered portion of working end 114 and the patient's tissue.

Insulative sheath 122 is applied around working end 114 so as to leave only a relatively small part of working end 114 exposed for use during electrosurgery. For example, insulative sheath 122 may cover the entire working end 114 except for about the last few centimeters. By way of example, insulative sheath 122 may cover most of working end 114 except for working surface 118C and between about 1 mm and about 5 mm of working surfaces 118A, 118B, or between about 2.5 mm and about 3 mm of working surfaces 118A, 118B. The exposed portions of working surfaces 118A, 118B, 118C can then be used to perform electrosurgery without electrical discharge between the rest of working end 114 and the patient's tissue.

Since insulative sheath 122 covers portions of working surfaces 118A, 118B and thereby only allows the exposed portions of working surfaces 118A, 118B to be used to perform electrosurgery, insulative sheath 122 provides depth control to working end 114. By way of example, if working surface 118A is 5 mm long and sheath 122 covers 2.5 mm of working surface 118A, only the exposed 2.5 mm of working surface 118A could create an incision. As a result, if a surgeon were to inadvertently try to press working surface 118A too deep into the tissue, insulative sheath 122 would prevent working surface 118A from making an incision that was deeper that 2.5 mm.

Insulative sheath 122 may be formed of any suitable material and positioned on electrode tip 108 in any suitable manner. For instance, insulative sheath 122 may be formed of an electrically insulative plastic tubing, such as PTFE, which is tightly fitted onto electrode tip 108. The insulative plastic tubing may be formed and positioned on electrode tip 108 through a variety of processes. In some embodiments, the insulative plastic tubing is formed in a cylindrical tube and then positioned on electrode tip 108. Once positioned on electrode tip 108, insulative sheath 122 may be tightly fitted and flattened thereon via a mechanical, thermal, molding, dipping, spraying, or heat shrink-fitting or press-fitting process so that the insulative plastic tubing is securely positioned on and generally conforms to the shape of electrode tip 108. In other embodiments, the insulative sheath is formed with a cross-sectional shape that generally corresponds to electrode tip 108 such that the insulative sheath can simply be slid on and secured to electrode tip 108 without requiring a shrink- or press-fitting process.

With specific attention to FIGS. 3 and 4, which illustrate close-up views of working end 114 and insulative sheath 122, certain aspects of insulative sheath 122 will be discussed. As noted elsewhere herein, electrode tips with insulative sleeves commonly create resistance to the movement of the electrode tip through tissue as a result of the tissue getting caught on the insulative sleeves. Insulative sheath 122 is designed to limit or prevent tissue from getting caught thereon, thereby reducing resistance to the movement of electrode tip 108 through tissue.

Figure 3:
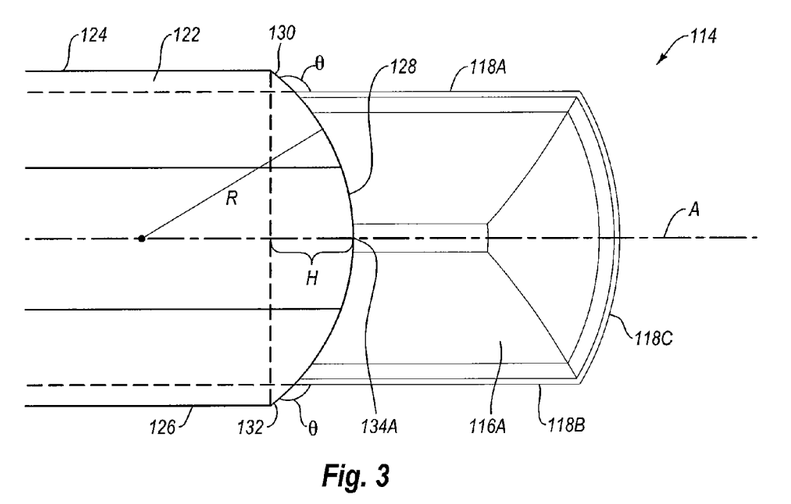
FIG. 3 illustrates a close-up view of the working end of the electrode tip of FIG. 2.
Figure 4:
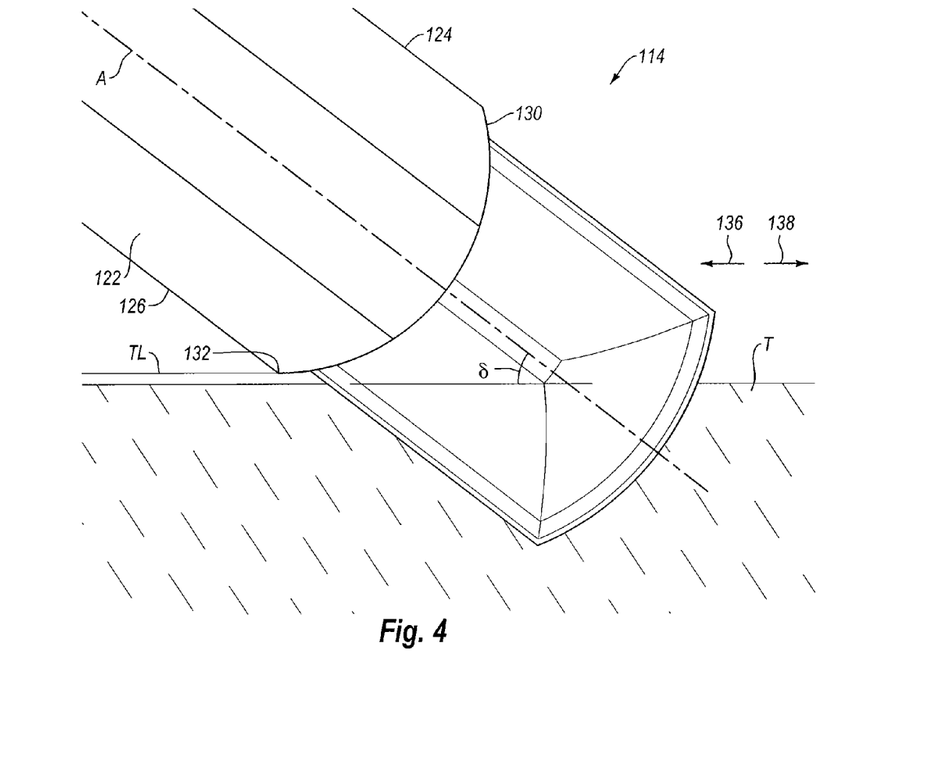
FIG. 4 is another close-up view of the working end of the electrode tip of FIG. 2, illustrating the electrode tip being used to cut tissue.

As shown in FIGS. 3 and 4, insulative sheath 122 includes a first side 124, a second side 126, and a leading edge 128. First side 124 covers the proximal portion of working surface 118A (e.g., the portion of working surface 118A closest to connection end 112) while leaving exposed the distal portion of working surface 118B (e.g., the portion of working surface 118A furthest from connection end 112). First side 124 is also generally parallel to working surface 118A. Similarly, second side 126 covers the proximal portion of working surface 118B while leaving the distal portion exposed. Also, second side 126 is generally parallel to working surface 118B.

Leading edge 128 extends between first side 124 and second side 126 and across major surfaces 116A, 116B of working end 114. In the illustrated embodiment, leading edge 128 includes first and second ends 130, 132 that meet first and second sides 124, 126, respectively. Between first and second ends 130, 132, leading edge 128 is generally arcuate and includes peaks 134A, 134B. As can be seen, peak 134A is disposed next to major surface 116A and peak 134B is disposed next to major surface 116B. Peaks 134A, 134B are disposed axially along axis A closer to working surface 118C than first and second ends 130, 132.

The arcuate shape of leading edge 128 is designed to provide the resistance reducing characteristics of insulative sheath 122. As shown in FIG. 3, leading edge 128 has a radius R so that first and second ends 130, 132 each form an obtuse angle θ with the exposed portion of respective working surfaces 118A, 118B. As will be understood by one of skill in the art, angle θ in the present embodiment is a result of radius R. Angle θ can, therefore, be changed by increasing or decreasing radius R of leading edge 128. More specifically, increasing radius R of leading edge 128 will decrease the value of angle θ while decreasing radius R of leading edge 128 will increase the value of angle θ.

Radius R, and thus the value of angle θ, can be selected based on various factors. For instance, radius R may be selected so that a tangent line TL at first end 130 or second end 132 (FIG. 4 illustrates tangent line TL at second end 132) of leading edge 128 is generally parallel to the surface of the tissue T being cut. Shaping leading edge 128 so that first and second ends 130, 132 have tangent lines TL that are generally parallel to the tissue T being cut gives leading edge 128 a profile that allows leading edge 128 to pass over tissue T minimal or no friction. More specifically, as shown in FIG. 4, having a tangent line TL at first or second ends 130, 132 that is generally parallel to tissue T allows leading edge 128 to slide or otherwise pass over tissue T (in the direction of arrows 136, 138) without tissue T getting caught on leading edge 128 or between leading edge 128 and working surfaces 118A, 118B.

Due to variations in surgical procedures and individual preferences of surgeons, different values for radius R may be required to create a tangent line TL that is generally parallel to the surface of the tissue T being cut. More specifically, some surgeons may hold electrode tip 108 at a steeper or shallower angle δ relative to tissue T (see FIG. 4) than other surgeons. Accordingly, the value of radius R can be selected so that a tangent line TL at first or second end 130, 132 will still be generally parallel to the tissue T when electrode tip 108 is held at different angles. By way of example, if electrode tip 108 were held so that angle δ was about 62°, radius R would need to be about 0.125 inches to create a tangent line TL at first or second end 130, 132 that is generally parallel to tissue T. If, however, electrode tip 108 were held so that angle δ was about 76°, radius R would need to be about 0.200 inches to create a tangent line TL at first or second end 130, 132 that is generally parallel to tissue T. Similarly, if electrode tip 108 were held so that angle δ was about 38°, radius R would need to be about 0.075 inches to create a tangent line TL at first or second end 130, 132 that is generally parallel to tissue T. Likewise, if electrode tip 108 were held so that angle δ was about 10°, radius R would need to be about 0.060 inches to create a tangent line TL at first or second end 130, 132 that is generally parallel to tissue T.

In light of the above discussion, it will be recognized that angle θ increases as radius R decreases. It will also be recognized that there will be less friction between leading edge 128 and tissue T as angle θ increases. More specifically, as angle θ increases, there will be less contact between leading edge 128 and tissue T, thus minimizing the friction therebetween. Increasing angle θ will also allow electrode tip 108 to be used at a variety of angles δ without creating friction between leading edge 128 and tissue T. Thus, while it may appear that the optimal configuration for insulative sheath 122 would be with leading edge 128 having a minimal radius R, as discussed below, minimizing radius R is not necessarily optimal.

The height H of leading edge 128 is another factor that may be considered in determining the desired value of radius R, and thus the value of angle θ. As is understood, height H is the distance between peaks 134A, 134B and a line that extends directly between first and second ends 130, 132), as shown in FIG. 3. As radius R changes, height H also changes. By way of example, height H would be about 0.015 inches when radius R is about 0.125 inches. When radius R is about 0.200 inches, height H is about 0.009. Similarly, when radius R is about 0.075 inches, height H is about 0.029 inches. Likewise, when radius R is about 0.060 inches, height H is about 0.052 inches. Thus, height H increases as radius R decreases. If height H becomes too long, however, there is a potential for insulative sheath 122 to flare or peel away from working end 114. That is, the strength of insulative sheath 122 between first and second ends 130, 132 and peaks 134A, 134B may not be sufficient to prevent flaring or peeling when height H is too long.

Accordingly, it is desirable to balance radius R, and thus angel θ, with height H to ensure that insulative sheath 122 has sufficient structural strength to prevent flaring or peeling of leading edge 128. It has been found that a PTFE sheath may have sufficient structural strength to prevent flaring or peeling of leading edge 128 with a height H up to about 0.052 inches (and a corresponding radius R of up to about 0.060. However, a height H that is about 0.052 inches would require electrode tip 108 to be held at a relatively shallow angle δ of about 10° so that the tangent line TL would be generally parallel to tissue T. Height H may be decreased to about 0.029 inches (by increasing radius R to about 0.075 inches) so that electrode tip 108 could be held at an angle δ of about 38° and making tangent line TL generally parallel to tissue T. Height H could be further decreased to about 0.015 inches (by increasing radius R to about 0.125 inches), which would allow electrode tip 108 to be held at an angle δ of about 62° so the tangent line TL would be generally parallel to tissue T. Height H may be reduced even further to about 0.009 inches (by increasing radius R to about 0.200 inches), which would allow electrode tip 108 to be held at an angle δ of about 76° so that the tangent line TL would be generally parallel to tissue T. The foregoing combinations are provided merely by way of example. Height H may be greater or smaller than the values explicitly discussed herein.

Figure 5:
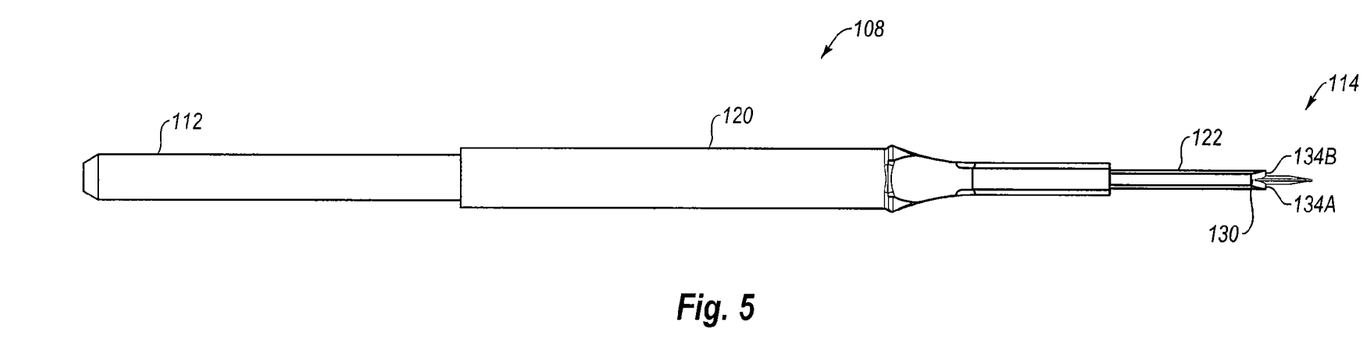
FIG. 5 illustrates a right side view of the electrode tip of FIG. 2, with the left side being a mirror image thereof.
Figure 6:
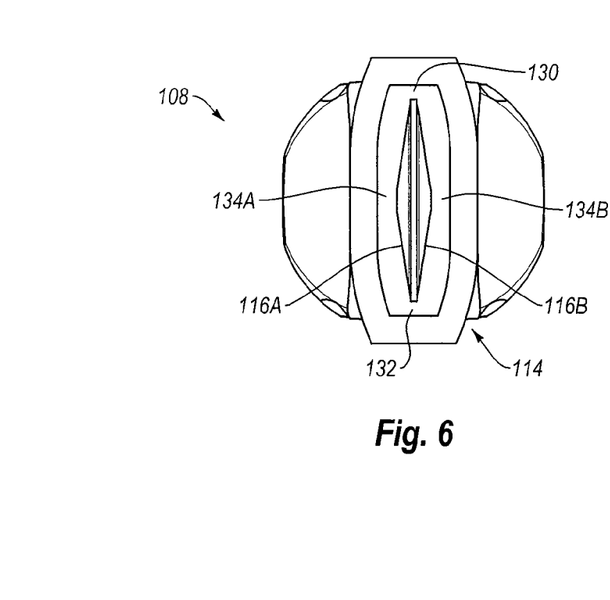
FIG. 6 illustrates a first end view of the electrode tip of FIG. 2.
Figure 7:
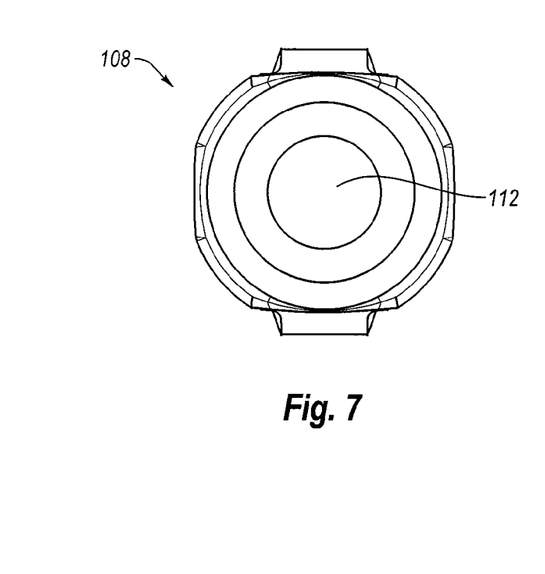
FIG. 7 illustrates a second end view of the electrode tip of FIG. 2.

FIGS. 5-7 illustrate various alternative views of electrode tip 108. Specifically, FIG. 5 illustrates a right side view of electrode tip 108. The left side view of electrode tip 108 is a mirror image of the right side view. As seen in FIG. 5, peaks 134A, 134B are disposed on opposing sides of working end 114 and are positioned further away from connection end 112 than first and second ends 130, 132. FIG. 6 is an end view of electrode tip 108 showing working end 114. FIG. 7 is also an end view of electrode tip 108, but showing connection end 112.

While FIGS. 1-7 illustrate leading edge 128 as having a generally arcuate shape, it will be understood that leading edge 128 may have a variety of different shapes and configurations without departing from the spirit or scope of the present invention. By way of example, leading edge 128 may be elliptical, triangular, trapezoidal, polygonal, symmetric, or asymmetric, so long as leading edge 128 performs the functions discussed herein. Additionally, while FIGS. 1-7 illustrate peaks 134A, 134B being offset an equal distance from first and second ends 130, 132, it will also be understood that peaks 134A, 134B may be offset different distances from first and second ends 130, 132. For instance, the axial distance between peaks 134A, 134B and first end 130 may be different than the axial distance between peaks 134A, 134B and second end 132. Likewise, first and second ends 130, 132 may be axially offset from one another. Similarly, peaks 134A, 134B may be axially offset from one another.

Turning attention to FIGS. 8-15, an alternative embodiment of an electrode tip 150 is illustrated. Electrode tip 150 is similar or identical to electrode tip 108 except for the configuration of the insulative sheath. Specifically, electrode tip 150 includes a main body having a connection end 152 and a working end 154. Like working end 114, working end 154 has two opposing major surface 156A, 156B, opposing working surfaces 158A, 158B, and working surface 158C. Working surfaces 158A, 158B, 158C can be relatively blunt, shaped, or sharpened. Additionally, working end 154 may take other forms, including having a needle, loop, ball, or laparoscopic electrode configuration.

Figure 8:
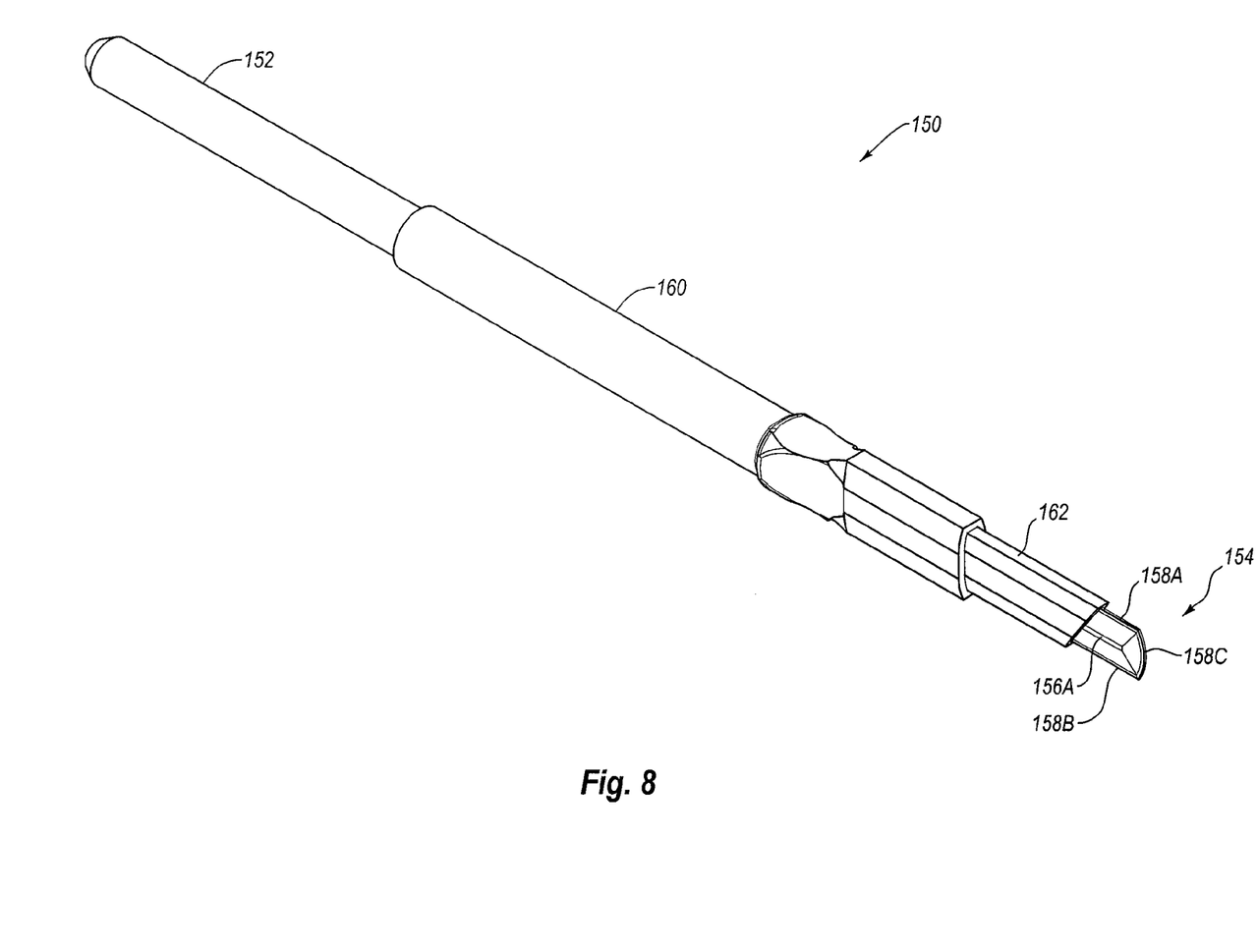
FIG. 8 illustrates a perspective view of another exemplary embodiment of an electrode tip for use in the electrosurgical system of FIG. 1 to cut tissue and cauterize blood vessels.

Electrode tip 150 also includes a sleeve fitting 160 and an optional coating of non-stick and/or insulating material that covers a surface of electrode tip 150. An insulative sheath 162 is also advantageously disposed on a portion of electrode tip 150. Like insulative sheath 122, insulative sheath 162 covers a portion of working end 154 in order to provide an insulative barrier between the covered portion of working end 154 and the patient's tissue. Insulative sheath 162 allows for the exposed portion of working end 154 to be used to perform electrosurgery without communicating electrical energy across insulative sheath 162 between the covered portion of working end 154 and the patient's tissue. Insulative sheath 162 may be formed of any suitable material and positioned on electrode tip 150 in any suitable manner, including the manner discussed above in connection with insulative sheath 122.

With specific attention to FIGS. 9 and 10, which illustrate close-up views of working end 154 and insulative sheath 162, certain aspects of insulative sheath 162 will be discussed. As noted elsewhere herein, electrode tips with insulative sleeves commonly create resistance to the movement of the electrode tip through tissue as a result of the tissue getting caught on the insulative sleeves. Insulative sheath 162 is designed to limit or prevent tissue from getting caught thereon, thereby reducing resistance to the movement of electrode tip 150 through tissue.

Figure 9:
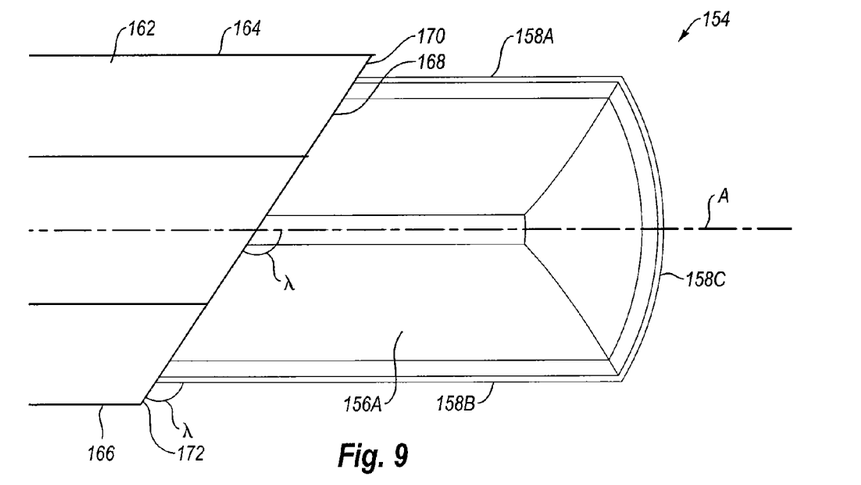
FIG. 9 illustrates a close-up view of the working end of the electrode tip of FIG. 8.
Figure 10:
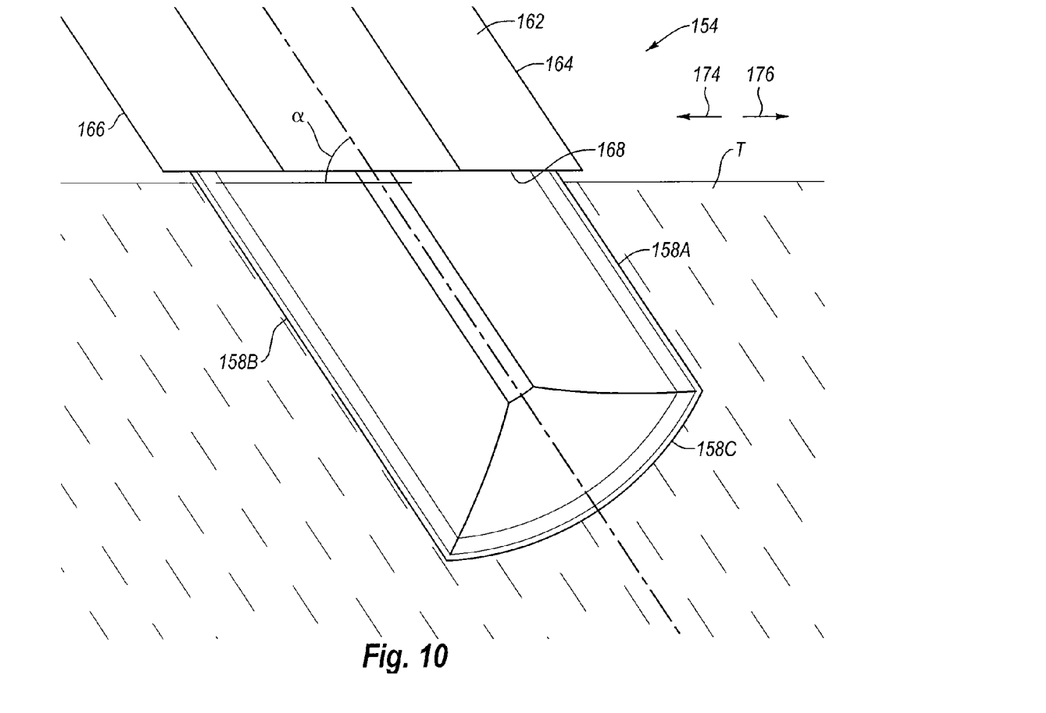
FIG. 10 is another close-up view of the working end of the electrode tip of FIG. 8, illustrating the electrode tip being used to cut tissue.

As shown in FIGS. 9 and 10, insulative sheath 162 includes a first side 164, a second side 166, and a leading edge 168. First side 164 covers the proximal portion of working surface 158A (e.g., the portion of working surface 158A closest to connection end 152) while leaving exposed the distal portion of working surface 188B (e.g., the portion of working surface 158A furthest from connection end 112). First side 164 is also generally parallel to working surface 158A. Similarly, second side 166 covers the proximal portion of working surface 158B while leaving the distal portion exposed. Also, second side 166 is generally parallel to working surface 158B.

Leading edge 168 extends between first side 164 and second side 166 and across major surfaces 156A, 156B of working end 154. In the illustrated embodiment, leading edge 168 includes first and second ends 170, 172 that meet first and second sides 164, 166, respectively. Leading edge 168 extends between first and second sides 164, 166 at an obtuse angle $\lambda$ relative to a longitudinal axis A of electrode tip 150. In other words, first and second ends 170, 172 are axially offset from one another so that leading edge forms angle $\lambda$.

The angled orientation of leading edge 168 is designed to reduce resistance to the movement of electrode tip 150 through tissue. More specifically, by angling leading edge 168 relative to longitudinal axis A, leading edge 168 can be oriented generally parallel to the surface of tissue T being cut, thereby substantially preventing tissue from getting caught on leading edge 168 or between leading edge 168 and a working surface, such as working surface 158B. For instance, as shown in FIG. 10, leading edge 168 is oriented generally parallel to the surface of Tissue T so that tissue does not get caught on leading edge 168 as the exposed portions of working end 154 is passed through tissue T in the directions of arrows 174, 176.

Angle $\lambda$ may be selected based upon the particular needs of a specific procedure or the preferences of individual surgeons. For instance, some surgeons may hold electrode tip 150 at a steeper angle $\alpha$ relative to the surface of tissue T than others. In such a case, angle $\lambda$ may be decreased so that leading edge 168 is generally parallel to the surface of tissue T when in use. Alternatively, angle $\lambda$ may be increased to accommodate surgeons that hold electrode tip 150 at a shallower angle $\alpha$. While angle $\lambda$ may be substantially any obtuse angle, the benefits of the present invention may be realized when angle $\lambda$ is between about 100° and about 160°, between about 115° and about 140°, and or about 120°.

As can be seen in the Figures, angle $\alpha$ and angle $\lambda$ are generally supplementary angles. Accordingly, and by way of non-limiting example, for surgeons that prefer to hold electrode tip 150 so that angle $\alpha$ is about 60°, angle $\lambda$ can be about 120°. In light of this discussion, it will be understood that so long as angle $\alpha$ and angle $\lambda$ are generally supplementary angles, leading edge 168 will always be generally parallel to the surface of tissue T. Keeping leading edge 168 generally parallel to the surface of tissue T minimizes the friction therebetween. Nevertheless, electrode tip 150 may be held at a shallower angle $\alpha$ without too significantly increasing any friction between leading edge 168 and tissue T. That is, electrode tip 150 may be held at an angle $\alpha$ such that second end 172 of leading edge 168 is closer to tissue T than first end 170. As discussed herein, the obtuse angle $\lambda$ between second end 172 and working surface 158B allows leading edge 168 to pass over tissue T without tissue T getting caught on leading edge 168 or between leading edge 168 and working surface 158B. Thus, angles $\alpha$ and $\lambda$ may be, but are not necessarily supplementary angles.

The angled configuration of leading edge 168 can also provide working end 154 with the functionality of two electrode tips in a single device. More specifically, because leading edge 168 is angled across working end 154, the exposed portions of working surfaces 158A, 158B are different lengths. As a result, a surgeon may use working surface 158A to perform certain types of incisions, such as shallow or delicate incisions. The surgeon may then turn electrode tip 150 over and use working surface 158B to perform other types of incisions, such as deeper incisions.

The specific lengths of the exposed portions of working surfaces 158A, 158B may be selected based on the preferences of surgeons or the needs in particular procedures. As will be understood, the relative lengths of the exposed portions of working surfaces 158A, 158B will be dependent on the angle $\lambda$ of leading edge 168. The larger angle $\lambda$ is, the greater the difference in the lengths of working surfaces 158A, 158B will be.

By way of example, insulative sheath 162 may cover most of working end 154 except for working surface 158C and between about 1 mm and about 5 mm of working surfaces 158A, 158B, or between about 2.5 mm and about 3 mm of working surfaces 158A, 158B. For instance, in one embodiment, insulative sheath 162 covers working end 154 except for working surface 158C, about 2 mm of working surface 158A, and about 5 mm of working surface 158B. In another embodiment, insulative sheath 162 covers working end 154 except for working surface 158C, about 2.5 mm of working surface 158A, and about 5 mm of working surface 158B. In yet another embodiment, insulative sheath 162 covers working end 154 except for working surface 158C, about 3 mm of working surface 158A, and about 4 mm of working surface 158B.

Figure 11:
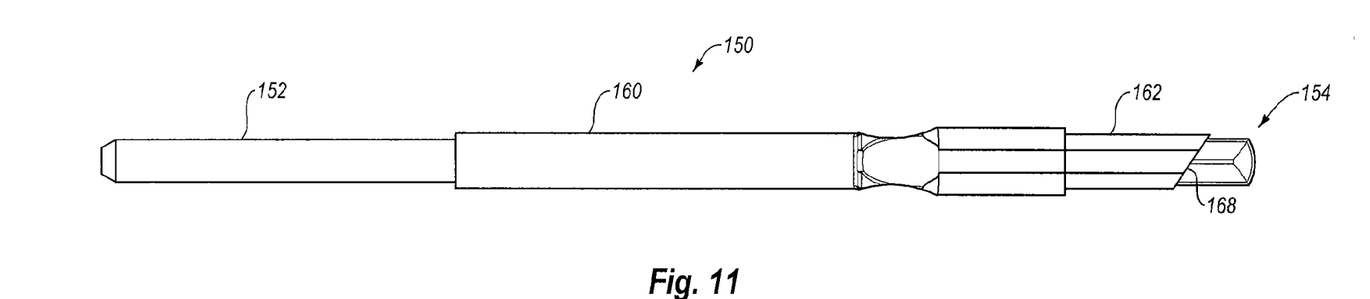
FIG. 11 illustrates a top view of the electrode tip of FIG. 8, with the bottom being a mirror image thereof.
Figure 12:
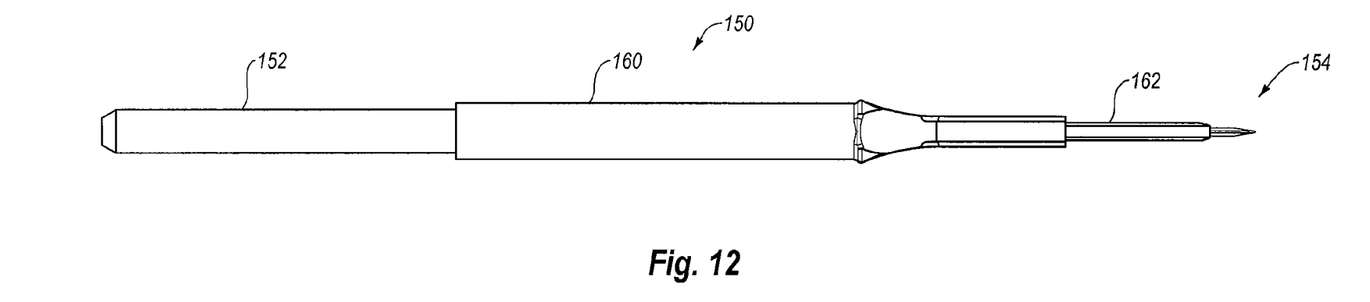
FIG. 12 illustrates a right side view of the electrode tip of FIG. 8.
Figure 13:
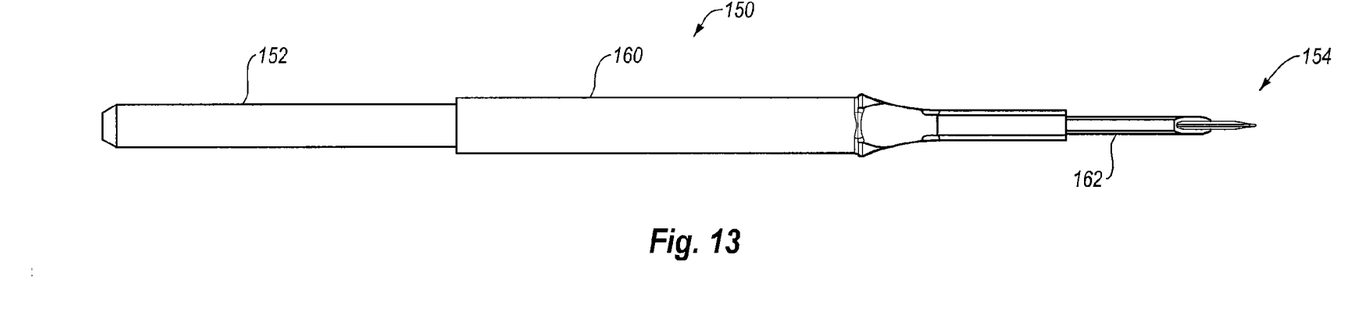
FIG. 13 illustrates a left side view of the electrode tip of FIG. 8.
Figure 14:
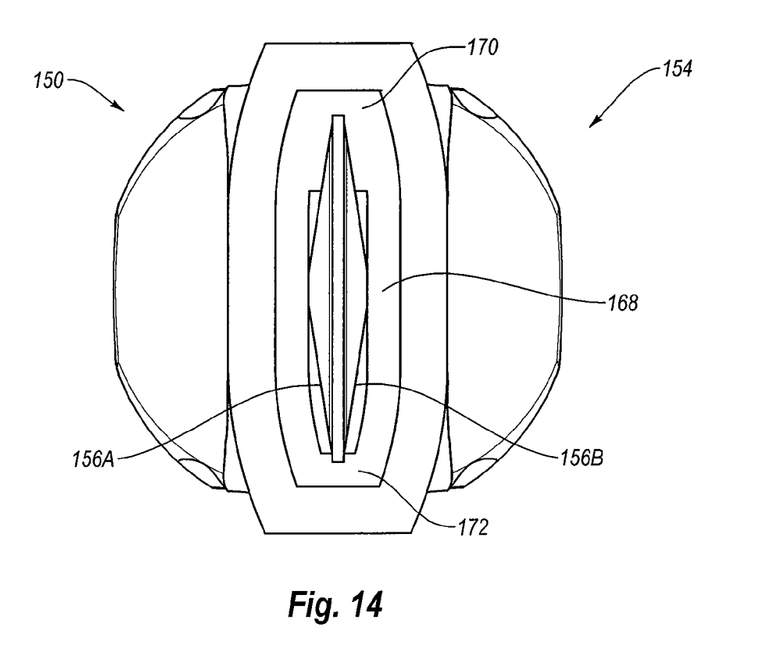
FIG. 14 illustrates a first end view of the electrode tip of FIG. 8.
Figure 15:
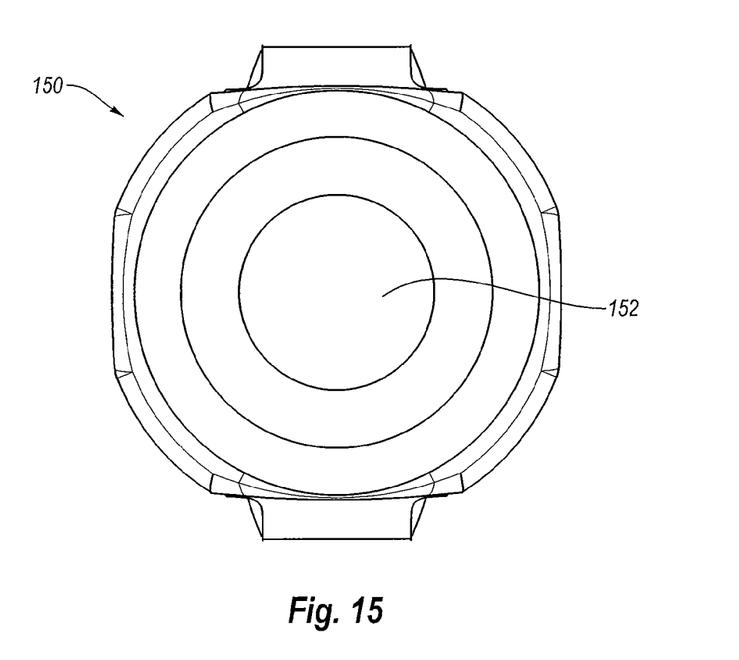
FIG. 15 illustrates a second end view of the electrode tip of FIG. 8.

FIGS. 11-15 illustrate various alternative views of electrode tip 150. Specifically, FIG. 11 illustrates a top view of electrode tip 150. The bottom view of electrode tip 150 is a mirror image of the top view. FIG. 12 is a right side view of electrode tip 108 and FIG. 13 is a left side view of electrode tip 150. FIG. 14 is an end view of electrode tip 150 showing working end 154. FIG. 15 is also an end view of electrode tip 150, but showing connection end 152.

Figure 16:
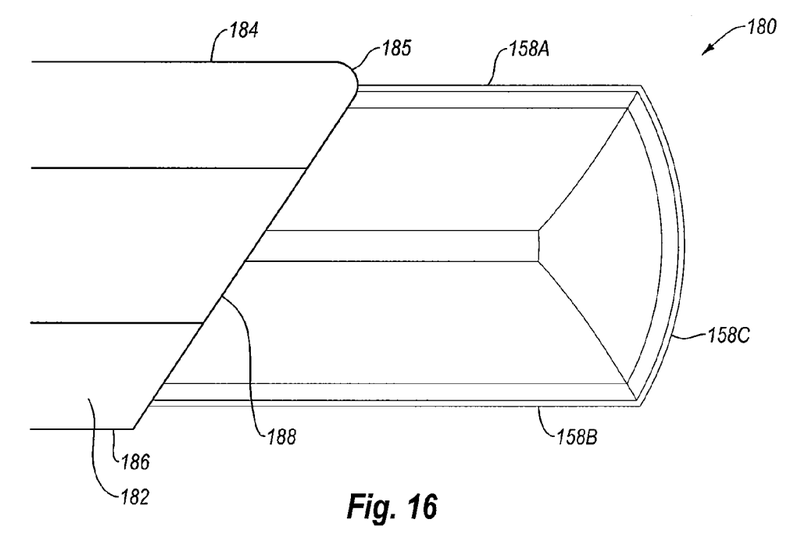
FIG. 16 illustrates a perspective view of yet another exemplary embodiment of an electrode tip for use in the electrosurgical system of FIG. 1 to cut tissue and cauterize blood vessels.

Attention is now directed to FIG. 16, which illustrates the working end 180 of an electrode tip that is similar in most respects to working end 154 of FIGS. 8-9. More specifically, working end 180 includes working surfaces 158A, 158B, 158C and an insulative sheath 182. Insulative sheath 182 includes a first side 184, a second side 186, and a leading edge 188. On electrode tip 150, first side 164 and leading edge 168 meet at a point, with first side 164 and leading edge 168 forming an acute angle. Although first side 184 and leading edge 188 still form an acute angle on working end 180, first side 184 and leading edge 188 do not meet at a point. Rather, the area 185 where first side 184 and leading edge 188 meet is rounded. By rounding area 185, tissue is less likely to get caught on leading edge 188 or between area 185 and working surface 158A. More specifically, rounding area 185 means that a tangent line on area 185 that is next to tissue being cut will more likely be generally parallel to the surface of the tissue. As a result, the tissue will be less likely to get caught on insulative sheath 182.

Figure 17:
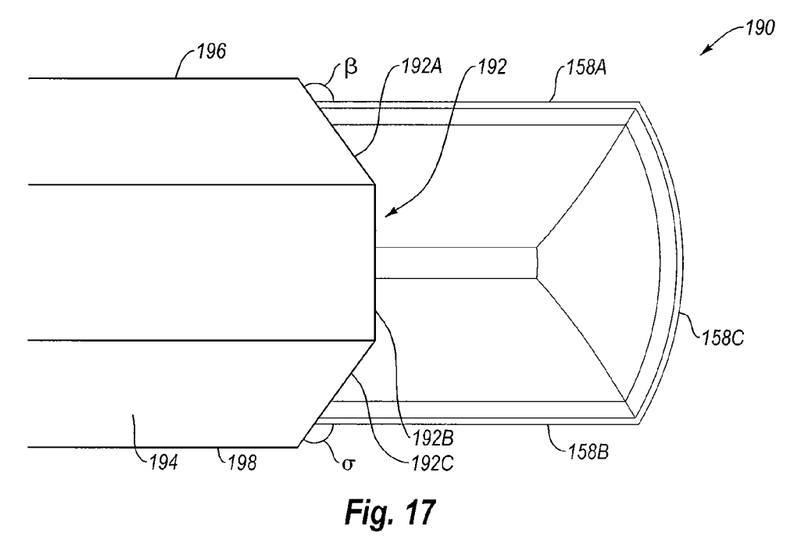
FIG. 17 illustrates a perspective view of still yet another exemplary embodiment of an electrode tip for use in the electrosurgical system of FIG. 1 to cut tissue and cauterize blood vessels.

FIG. 17 illustrates still yet another embodiment of the present invention. Specifically, FIG. 17 illustrates a working end 190 of an electrode tip. Working end 190 is similar to the previously discussed electrode tips except that the leading edge 192 of the insulative sheath 194 has a different configuration than those previously described. Like the other insulative sheaths discussed herein, insulative sheath 194 has a first side 196 and a second side 198, with leading edge 192 extending therebetween.

Leading edge 192 is generally trapezoidal in shape and includes three sections 192A, 192B, 192C. Section 192B is oriented generally perpendicular to working surfaces 158A, 158B, while sections 192A, 192C are angled relative to working surfaces 158A, 158B. Specifically, section 192A is oriented to form an obtuse angle β with working surface 158A and section 192B is oriented to form an obtuse angle σ with working surface 158B. As discussed herein, forming an obtuse angle between the leading edge of an insulative sheath and the adjacent working surfaces limits the resistance resulting from the interaction of the leading edge and the tissue being cut. It will be understood that angles β and σ may be similar or identical to angles θ and λ discussed above. Additionally, angles β and σ may be equal to one another or they may be different from one another. Likewise, the opposing ends of leading edge 192 may be axially offset from one another as discussed in connection with the other embodiments described herein. Furthermore, section 192B may not be perpendicular to working surfaces 158A, 158B. As a result, the area where sections 192A, 192B meet may be axially offset from the area where sections 192B, 192C meet.

Working end 190 includes two angled sections (i.e., sections 192A, 192C) on leading edge 192 so that either of working surfaces 158A, 158B may be used to cut tissue without tissue getting caught on either end of leading edge 192. For instance, working end 190 may be held at an orientation similar to that shown in FIGS. 4 and 10 so that working surface 158C can be used to cut tissue. In such an orientation, section 192C would be generally parallel to the surface of the tissue being cut and would, therefore, create minimal resistance therebetween. Similarly, working end 190 may be turned over so that working surface 158A can be used to cut tissue while being held at an orientation similar to that shown in FIGS. 4 and 10. Like section 192C, in such an orientation section 192A would be generally parallel to the surface of the tissue being cut and would, therefore, create minimal resistance therebetween.

As noted herein, the present invention may take the form of or be incorporated into other types of surgical systems. For instance, a surgical scalpel may be fitted with a protective sheath similar or identical to the sheaths discussed herein. Such a sheath may be formed of an insulative or non-insulative material. The sheath may include a leading edge that is similar to the leading edges described above and shown in the Figures. For instance, the leading edge may form an obtuse angle with a sharpened working surface of the scalpel so as to provide the functionality described herein. Likewise, the leading edge may have a similar shape to the leading edges described above and shown in the Figures.

The present invention may also be incorporated into other energy based systems. Such energy based systems may include thermal systems that transfer or utilize thermal energy to perform surgical procedures. A thermal based surgical system may include an instrument that has a working surface that is applied to tissue to transfer or otherwise utilize the thermal energy to perform surgical procedures on the tissue. As with the previously described embodiments, the thermal instrument may include a sheath that performs the functionality described herein. Specifically, the sheath may prevent the transfer of thermal energy to the tissue across the sheath. The leading edge of the sheath may also be designed as described herein to limit the friction between the sheath and the tissue.

The present invention may also be incorporated into still other surgical systems, such as fluid based surgical systems. Such fluid based systems may include an instrument that delivers a fluid to tissue to perform surgical procedures on the tissue. As with the previously described embodiments, the instrument may include a sheath that performs the functionality described herein. For instance, the sheath may prevent the delivery of fluid from a portion of the instrument or may direct the fluid in a desired direction. The sheath may include a leading edge similar to those described herein to limit the friction between the sheath and the tissue.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A monopolar electrosurgical device adapted for use in performing operative procedures, the monopolar electrosurgical device comprising:
a main body having a connection end and a working end, the working end having a proximal end adjacent the connection end, a distal end opposite the connection end, a first major surface, a second, opposing major surface, a first side joining the first major surface and the second, opposing major surface, a second, opposing side joining the first major surface and the second, opposing major surface, and at least one of the first side and second, opposing side forming one or more working surfaces adapted to be applied to patient tissue for performing operative procedures thereupon, at least one of the one or more working surfaces extending between the proximal end and the distal end of the working end; and
an electrically insulative sheath disposed around at least a portion of the working end such that the sheath covers at least a first portion of the at least one of the one or more working surfaces and leaves exposed a second portion of the at least one of the one or more working surfaces, at least a portion of the connection end extending proximally out of the sheath, the sheath having a leading edge that extends away from the working end at the at least one of the one or more working surfaces such that the junction between the leading edge and the at least one of the one or more working surfaces forms a generally obtuse angle, the leading edge being in generally uniform contact with the first major surface, the second, opposing major surface, the first side, and the second, opposing side of the working end such that substantially no void exists between the leading edge and the first major surface, the second, opposing major surface, the first side, and the second, opposing side of the working end.

2. The monopolar electrosurgical device of claim 1, wherein the one or more working surfaces comprise a first working surface disposed on the first side of the working end and a second working surface disposed on the second, opposing side of the working end.

3. The monopolar electrosurgical device of claim 1, wherein the sheath includes a first side disposed adjacent to the first side of the working end and a second side disposed adjacent the second, opposing side of the working end, wherein the leading edge of the sheath extends between the first and second sides of the sheath.

4. The monopolar electrosurgical device of claim 1, wherein the portions of the leading edge of the sheath that extend across the first major surface and the second, opposing major surface each have a general shape that is at least one of arcuate, elliptical, triangular, trapezoidal, or polygonal.

5. The monopolar electrosurgical device of claim 1, wherein the leading edge includes a first end disposed adjacent the first side of the working end, a second end disposed adjacent the second side of the working end, and at least one peak disposed between the first and second ends.

6. The monopolar electrosurgical device of claim 5, wherein the one or more working surfaces comprise a first working surface disposed on the first side of the working end and a second working surface disposed on the second, opposing side of the working end, and wherein the junction between the first end of the leading edge and the first working surface forms a generally obtuse angle and the junction between the second end of the leading edge and the second working surface forms a generally obtuse angle.

7. The monopolar electrosurgical device of claim 5, wherein the working end has a longitudinal axis extending between the proximal and distal ends of the working end and the at least one peak is axially offset along the longitudinal axis from the first and second ends of the leading edge.

8. The monopolar electrosurgical device of claim 7, wherein the first and second ends of the leading edge are axially offset from one another along the longitudinal axis.

9. The monopolar electrosurgical device of claim 7, wherein the at least one peak is axially offset along the longitudinal axis from the first and second ends of the leading edge by a distance of between about 0.015 inches and about 0.029 inches.

10. The monopolar electrosurgical device of claim 7, wherein the at least one peak is axially offset along the longitudinal axis from the first and second ends of the leading edge by a distance of between about 0.009 inches and about 0.052 inches.

11. The monopolar electrosurgical device of claim 1, wherein the leading edge has a radius of between about 0.060 inches and about 0.200 inches.

12. The monopolar electrosurgical device of claim 1, wherein the leading edge has a radius of between about 0.075 inches and about 0.125 inches.

13. The monopolar electrosurgical device of claim 1, wherein the working end has a longitudinal axis and the leading edge extends across the working end from the first side to the second, opposing side, the leading edge forming a generally obtuse angle with the longitudinal axis.

14. The monopolar electrosurgical device of claim 13, wherein the leading edge includes a first end that forms a generally obtuse angle with at least one of the one or more working surfaces.

15. The monopolar electrosurgical device of claim 1, wherein the one or more working surfaces comprise a first working surface disposed on the first side of the working end and a second working surface disposed on the second, opposing side of the working end, and wherein the leading edge comprises a first section that forms a generally obtuse angle with the first working surface and a second section that forms a generally obtuse angle with the second working surface.

16. The monopolar electrosurgical device of claim 15, wherein the first section and the second section of the leading edge are oriented generally transversely to one another.

17. The monopolar electrosurgical device of claim 1, wherein the leading edge is asymmetrical across a longitudinal axis of the monopolar electrosurgical device.

18. The monopolar electrosurgical device of claim 1, wherein the monopolar electrosurgical device comprises an electrosurgical electrode tip adapted to communicate electrical energy to patient tissue.

19. A monopolar electrode tip adapted for use in performing electrosurgical operative procedures, the monopolar electrode tip comprising:
a main body, formed of a conductive material, adapted to be electrically connected to an electrosurgical generator to facilitate communication of electrical energy from the electrosurgical generator to the monopolar electrode tip, the main body comprising a connection end and a working end, the working end having a proximal end, a distal end, and first and second opposing working surfaces adapted to communicate the electrical energy from the main body to patient tissue for performing electrosurgical operative procedures thereupon, the first and second opposing working surfaces extending between the proximal and distal ends of the working end;

an electrically insulative sheath, formed of an electrically insulative material, disposed around at least a portion of the working end such that the insulative sheath covers at least a portion of each of the first and second opposing working surface and leaves exposed at least a portion of each of the first and second working surfaces, at least a portion of the connection end extending proximally out of the sheath the insulative sheath having a first side disposed adjacent the first working surface, a second side disposed adjacent the second working surface, and a leading edge extending between the first and second sides, the leading edge having a generally arcuate shape such that a first end of the leading edge forms a generally obtuse angle with the first working surface and a second end of the leading edge forms a generally obtuse angle with the second working surface, an interior surface of the sheath having a size and a shape that correspond to a cross-sectional size and shape of the working end such that the leading edge is in contact with the first working surface and the second working surface and such that substantially no void exists between the leading edge and the first working surface or between the leading edge and the second working surface.

20. The monopolar electrode tip of claim 19, wherein the leading edge comprises at least one peak that is offset from the first and second ends of the leading edge along a longitudinal axis of the monopolar electrode tip.

21. The monopolar electrode tip of claim 20, wherein the first and second ends of the leading edge are axially offset from one another along the longitudinal axis of the monopolar electrode tip.

22. The electrode tip of claim 19, wherein the at least one peak is offset from the first and second ends of the leading edge by a distance of about 0.015 inches and the leading edge has a radius of about 0.125 inches.

23. The surgical device of claim 19, wherein the insulative sheath is formed of PTFE.

24. A monopolar electrosurgical device adapted for use in performing operative procedures, the monopolar electrosurgical device comprising:
a main body having a connection end and a working end, the working end having first and second opposing sides that extend between proximal and distal ends of the working end, the first and second opposing sides defining respective first and second working surfaces that are adapted to be applied to patient tissue for performing operative procedures thereupon, the working end having a longitudinal axis that extends between the proximal and distal ends of the working end;
an electrically insulative sheath disposed around at least a portion of the working end such that the sheath covers at least a portion of each of the first and second working surfaces and leaves exposed at least a portion of each of the first and second working surfaces, at least a portion of the connection end extending proximally out of the sheath the sheath having a first side disposed adjacent the first working surface, a second side disposed adjacent the second working surface, and a leading edge extending between the first and second sides of the sheath, the leading edge extending across the working end and forming a generally obtuse angle with the longitudinal axis and at the junction with each of the first and second working surfaces, an interior surface of the sheath having a size and a shape that correspond to a cross-sectional size and shape of the working end such that the leading edge is in uniform contact with the first working surface and the second working surface and such that substantially no void exists between the leading edge and the first working surface or between the leading edge and the second working surface.

25. The monopolar electrosurgical device of claim 24, wherein the leading edge includes a first end disposed adjacent the first working surface, the first end and the first working surface forming a generally obtuse angle.

* * * * *

UNITED STATES PATENT AND TRADEMARK OFFICE
CERTIFICATE OF CORRECTION

PATENT NO. : 9,168,092 B2  Page 1 of 1
APPLICATION NO. : 13/029434
DATED : October 27, 2015
INVENTOR(S) : Horner et al.

It is certified that error appears in the above-identified patent and that said Letters Patent is hereby corrected as shown below:

In The Specification

Column 3
Line 43, change "if" to --is--

Column 10
Line 30, change "angel" to --angle--

Column 11
Line 56, change "188B" to --158A--
Line 57, change "112" to --152--

Column 13
Line 20, change "108" to --150--
Line 58, change "192B" to --192C--

Signed and Sealed this
Twenty-ninth Day of March, 2016

Michelle K. Lee
*Director of the United States Patent and Trademark Office*